US 6,572,634 B2

(12) United States Patent
Koo

(10) Patent No.: US 6,572,634 B2
(45) Date of Patent: Jun. 3, 2003

(54) NOSE END ADJUSTING DEVICE

(76) Inventor: Myung H. Koo, 18622 Nottingham Ln., Rowland Heights, CA (US) 91748

( * ) Notice: Subject to any disclaimer, the term of this patent is extended or adjusted under 35 U.S.C. 154(b) by 134 days.

(21) Appl. No.: 09/850,567

(22) Filed: May 7, 2001

(65) Prior Publication Data

US 2002/0165476 A1 Nov. 7, 2002

(51) Int. Cl.$^7$ .............................................. A61M 29/00
(52) U.S. Cl. .................. 606/199; 606/204.45; 128/858
(58) Field of Search .................. 128/857, 858; 606/196, 198, 199, 201, 204.45

(56) References Cited

U.S. PATENT DOCUMENTS 2,202,748 A * 5/1940 Solo ...................... 606/204.45
2,265,387 A * 12/1941 McMillin ..................... 606/199
5,772,682 A * 6/1998 Yokomizo .............. 606/204.45
5,983,898 A * 11/1999 Doyle ......................... 128/858
6,383,207 B1 * 5/2002 Bergham ............... 606/204.45

* cited by examiner

*Primary Examiner*—Michael A. Brown
(74) *Attorney, Agent, or Firm*—Park & Sutton LLP; John K. Park

(57) ABSTRACT

A nose end adjusting device includes a first nostril projection having a first upper surface. The base connector has a recess and a vertical axis. The recess has a recess base and a recess gap. The recess base accepts the back of the septum of a nose, and the recess gap accepts the end of the septum of the nose. The vertical axis and the first upper surface form an angle α. When the first nostril projection is inserted into a first nostril of the nose, the first nostril projection applies pressure to the first nostril. The pressure causes the first nostril and the nose to be lowered.

7 Claims, 7 Drawing Sheets

NOSE END ADJUSTING DEVICE

BACKGROUND OF THE INVENTION

The present invention relates to a device for modifying the shape of the nose. More specifically, the invention relates to an improved device for raising, lowering or extending the shape of the nose.

Many individuals are unsatisfied with their nose. Some people have a nose that is too low, others have a nose that is too high, and for some people their nose is too flat. A large percentage of these individuals have a nose they would prefer to alter in shape and appearance. There are options available for altering the shape to the nose, including cosmetic surgery.

Cosmetic surgery often causes a significant change in the appearance of the nose. The surgery may be a more drastic change than the individual had anticipated. When overcorrections or errors occur in cosmetic surgery, the damage must be repaired or accepted. Repair can be emotionally frustrating, time consuming and expensive.

Accepting a botched surgery is emotionally challenging. The surgery results can create a nose with a worse appearance than originally, prior to the surgery. The tissue and nose structure can be soft and delicate, following an initial operation on the tissue, cartilage and septum of the nose. Performing a second re-constructive surgery on the nose can require the services to a cosmetic re-constructive specialist. Specialists are more expensive than the initial cosmetic surgeon and top quality specialists are often located in distant cities.

Cosmetic surgery is normally successful and the patients are fully satisfied with their new appearances. On the other hand, many people that would like to change the shape of their nose hesitate to have cosmetic surgery because of the possibility of a botched surgery. The possibility of being forced to accept a deformed nose causes a person to avoid the decision to alter the shape of their nose. Cosmetic surgery, as an option, is expensive and requires the services of a doctor. There is a need for a device that can modify the shape and appearance of a nose without surgery.

Therefore, there is a need for a device for altering the shape of the nose that an individual can use themselves, without the service of a physician. The device needs to perform the nose altering function, without cutting the tissue or cartilage in the nose. The device should be simple to use and easily inserted into the nose.

SUMMARY OF THE INVENTION

The nose end adjusting device fulfills the objective of a device for altering the shape of the nose without the service of a physician. An individual can use the nose end adjusting device in the comfort of their own home.

A second objective is performing the nose altering function, without cutting the tissue or cartilage in the nose. The invention can be made from rigid rubber or plastic. Surgery style cutting of the tissue is not necessary. The invention applies steady and continuous pressure to the tissue that gradually alters the shape of the nose.

Another objective is a device that is simple to use and easily inserted into the nose. The invention is very easy to position into the nose. Wearing the nose end adjusting device during the sleeping hours is particularly advantageous. The invention does not interfere with daytime activities, when used exclusively in the nighttime.

A nose end adjusting device includes a first nostril projection having a first upper surface and a second nostril projection having a second upper surface. The base connector has a recess and a vertical axis. The recess has a recess base and a recess gap. The base connector is attached to the first nostril projection and the second nostril projection. The recess base accepts the back of the septum of a nose and the recess gap accepts the end of the septum of the nose. The septum of the nose rests in the recess, which allows the first nostril projection and the second nostril projection to protrude into the nose.

The vertical axis and the first upper surface form an angle $\alpha$. The vertical axis and the second upper surface form an angle $\beta$. The angle $\alpha$ and angle $\beta$ are less than about ninety degrees. When the first nostril projection is inserted into a first nostril of the nose, the first nostril projection applies pressure to the first nostril. The pressure causes the first nostril and the nose to be lowered. The second nostril projection is inserted into a second nostril. The second nostril and the nose are lowered, when the second nostril projection applies pressure to the second nostril.

The first projection has a first opening and the second projection has a second opening. Air is inhaled and exhaled through the first opening and the second opening. The first projection and the second projection have sides with apertures. Air is inhaled and exhaled through the apertures. Apertures travel from the exterior of the device to the openings. Other apertures travel from the openings to the recess. In one embodiment, the angle $\alpha$ is about sixty degrees. In another embodiment, the angle $\alpha$ is about ninety degrees.

The nose end adjusting device can also be used for raising the nose. To raise the nose the vertical axis and the first upper surface form an angle $\alpha$, where the angle $\alpha$ is greater than about ninety degrees. The vertical axis and the second upper surface form an angle $\beta$, where the angle $\beta$ is greater than about ninety degrees. Pressure is applied by the first nostril projection so that the first nostril and the nose are raised. When the second nostril projection is inserted into a second nostril, the second nostril projection applies pressure to the second nostril. The second nostril and the nose are raised, by the pressure from the second nostril projection. In one version, the angle $\alpha$ is about one hundred and twenty degrees. In another version, the angle $\beta$ is about ninety degrees.

The first projection has a length 'L'. The length 'L' can be about 9/16 of an inch. The first opening has a width 'w'. The width 'w' can be about 3/8 of an inch. The recess base has a height 'h'. The height 'h' can be about 5/16 of an inch.

Typically the angle $\alpha$ is the same as the angle $\beta$, since the first nostril and the second nostril are usually altered in the same direction and angle. Some people have a nose where they would like the first nostril and the second nostril to be altered at different angles. One angle can be greater than ninety degrees to raise a nostril, while the other angle is less than ninety degrees to lower the other nostril. When the angles vary, the vertical axis and the first upper surface form an angle $\alpha$ and the vertical axis and the second upper surface form an angle $\beta$, where the angle $\alpha$ is different than the angle $\beta$.

Angle $\alpha$ can be about ninety degrees and the angle $\beta$ can be about ninety degrees, even though they are different angles. When the angles are about ninety degrees, the first nostril and the nose are extended, and the second nostril and the nose are extended. The first opening can be greater than three times the size of any aperture and the second opening can be greater than three times the size of any aperture.

When the nose is being raised the recess base does not have to be very deep, since the recess drops mostly below the base of the septum. In contrast, when the nose is being lowered the recess base needs to be very deep, since the recess rises and accepts a more significant portion of the base of the septum. The recess gap is fully open, so the recess gap can rise within the nostrils, high up on the tip of the septum without any interference from the structure of the base connector.

The first opening and the second opening individually can be greater than three times the size of an one of the apertures. The greatest amount of air is inhaled and exhaled through the first opening and the second opening, so they are larger than the apertures. The apertures provide added passageways for movement of the air during breathing.

Although the present invention is briefly summarized, a fuller understanding of the invention can be obtained from the following drawings, detailed description and appended claims.

DETAILED DESCRIPTION OF THE DRAWINGS

Figure 1:
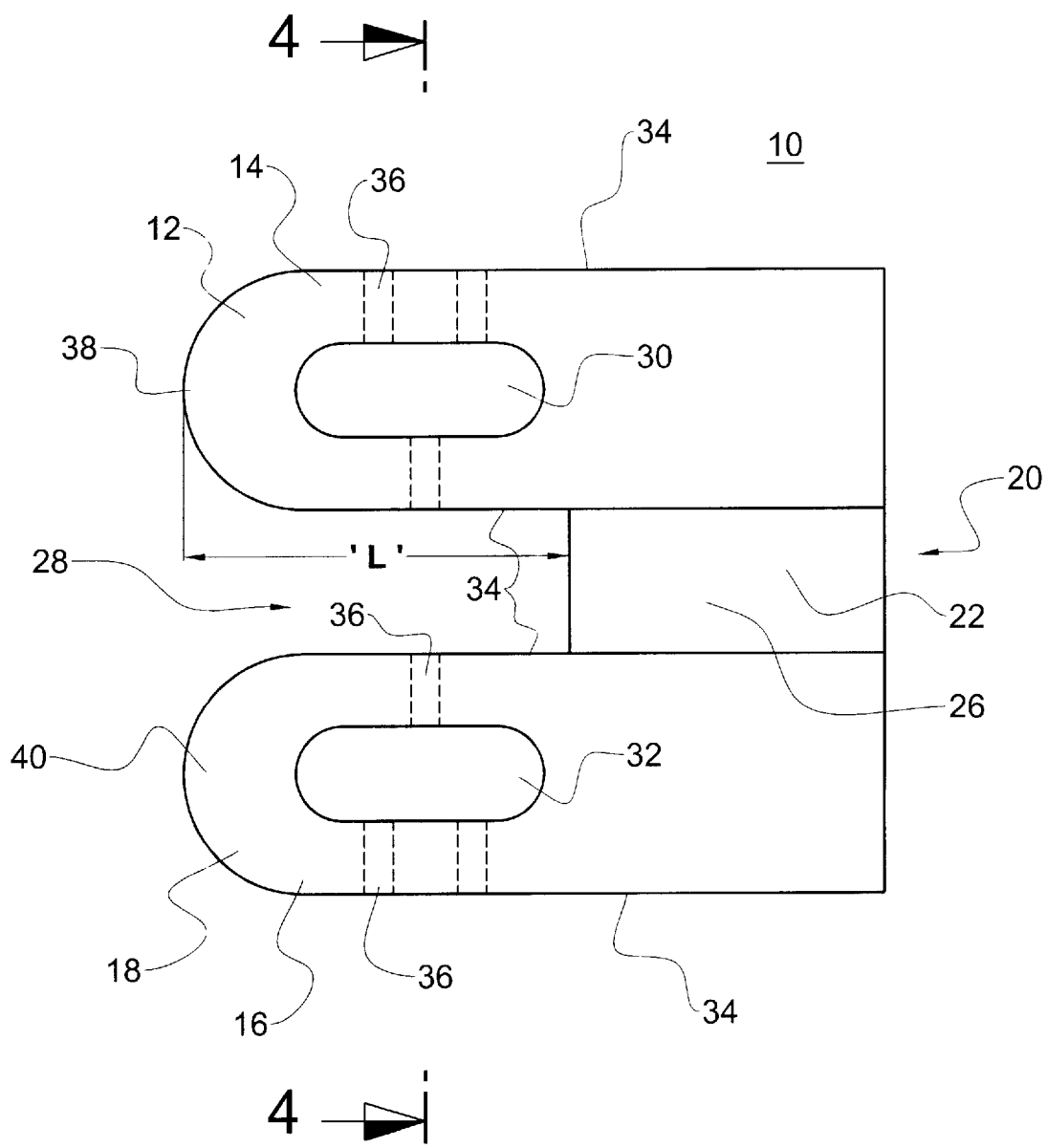
FIG. 1 is a top view of the nose end adjusting device.

Referring to FIGS. 1–10, the nose end adjusting device 10 is shown larger than actual size; a nose end adjusting device 10 includes a first nostril projection 12 having a first upper surface 14, and a second nostril projection 16 having a second upper surface 18. The base connector 20 has a recess 22 and a vertical axis 24. The recess 22 has a recess base 26 and a recess gap 28. The base connector 20 is attached to the first nostril projection 12 and the second nostril projection 16. The recess base 26 accepts the back of the septum 100 of a nose 102, and the recess gap 28 accepts the end of the septum 100 of the nose 102. The septum 100 of the nose 102 rests in the recess 22, which allows the first nostril projection 12 and the second nostril projection 16 to protrude into the nose 102.

The recess 22 includes both the recess base 26 and the recess gap 28. The recess base 26 is the indentation formed in the base connector 20 to receive the back of the septum 100 of the nose 102. The recess base 26 is an indentation from the top of the device 10. The recess base 26 is enclosed on the sides and bottom by the base connector 20. The recess gap 28 lies between the first nostril projection 12 and the second nostril projection 16. The recess gap 28 is fully open from the top of the device 10 to the bottom of the device 10.

The vertical axis 24 and the first upper surface 14 form an angle $\alpha$. The vertical axis 24 and the second upper surface 18 form an angle $\beta$. When the first nostril projection 12 is inserted into a first nostril 104 of the nose 102, the first nostril projection 12 applies pressure to the first nostril 104. The pressure causes the first nostril 104 and the nose 102 to be lowered, raised or extended depending on the angle. The second nostril projection 16 is inserted into a second nostril 106. The second nostril 106 and the nose 102 are lowered, raised or extended, when the second nostril projection 16 applies pressure to the second nostril 106.

The first nostril projection 12 has a first opening 30, and the second nostril projection 16 has a second opening 32. Air is inhaled and exhaled through the first opening 30 and the second opening 32. The first nostril projection 12 and the second nostril projection 16 have sides 34 with apertures 36. Air is inhaled and exhaled through the apertures 36.

The first nostril projection 12 has the first upper surface 14 and a first tip 38. The first tip 38 pushes against the inside of the first nostril 104 of the nose 102. Similarly, the second nostril projection 16 has a second tip 40, which applies pressure to the second nostril 106. The pressure applied by the first tip 38 moves and alters the position of the tissue. Continued usage of the nose end adjusting device 10, with consistent pressure applied to the nose 102, gradually alters the shape of the nose 102. Once the desired shape is achieved, the change can be maintained by periodically using the nose end adjusting device 10. The tissue has an elastic characteristic that tends to return the nose 102 to its original shape, after the nose 102 modification has occurred. Occasional use of the device 10 will counteract any propensity of the nose 102 to return to its original shape.

First nostril projections 12 and second nostril projections 16 with various lengths 'L' can be used over time. Initially a nostril projection with a shorter length 'L' can be used, which applies the desired amount of pressure to the nose 102. As the nose 102 begins to modify shape, the initial nostril projections 12, 16 will apply less pressure to the tissue. Then a subsequent device with first nostril projection 12 and the second nostril projection 16 having a longer length 'L' can be used to apply greater pressure. The subsequent device 10 will ultimately create a greater modification in the shape of the nose 102, than the initial device 10 is capable of performing. Length 'L' is distance from one of the tips 38, 40 to the point where the corresponding nostril projections 12, 16 intersects the base connector 20.

Figure 2:
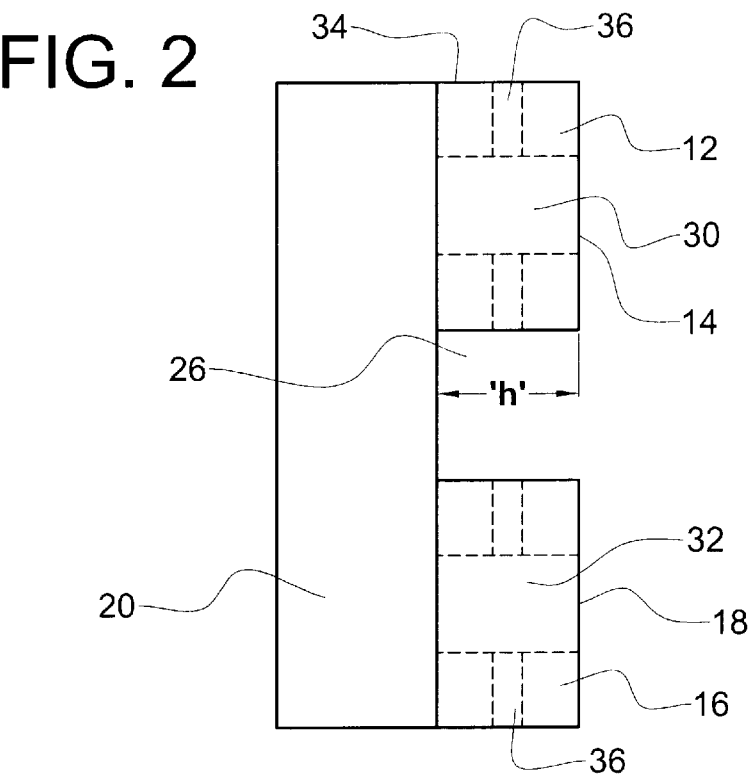
FIG. 2 is a front view of the device, with the openings and apertures shown in dashed lines.

Referring particularly to FIG. 1, that illustrates a top view of the device and FIG. 2 that shows a front view of the device 10. The first nostril projection 12 and the second nostril projection 16 are connected to the base connector 20. The first tip 38 of the first nostril projection 12 and the second tip 40 of the second nostril projection 16 can apply pressure to the inside of the nose 102. The base connector 20 has the recess 22. The recess 22 has the recess gap 28 and the recess base 26. The recess base 26 is formed by the base connector 20. The recess base 26 and the recess gap 28 are between the first nostril projection 12 and the second nostril projection 16. The recess gap 28 is in front of the recess base 26. The recess gap 28 provides an opening between the first nostril projection 12 and the second nostril projection 16, so that the first tip 38 and the second tip 40 can be positioned up inside the nose 102. The septum 100 near the nose end 108 is accepted by the recess gap 28. The first opening 30 and second opening 32 are shown in dashed lines in FIG. 2. The first opening 30 provides a passage way through the first nostril projection 12. The second opening 32 provides a passage way through the second nostril projection 16. The first nostril projection 12 and the second nostril projection 16 have sides 34 with apertures. The apertures, shown in dashed lines, allow additional air to be inhaled and exhaled through the first nostril projection 12 and the second nostril projection 16.

The first opening 30 and the second opening 32 provide a passage for breathing. The first opening 30 travels from the first upper surface 14 all the way through the first nostril projection 12, so there is an unobstructed passageway for inhaling and exhaling. The first opening 30 is positioned near the center of the first nostril projection 12. The second opening 32 travels from the second upper surface 18 through the second nostril projection 16. The second opening 32 is positioned near the center of the second nostril projection 16. The shape and function of the first opening 30 and the second opening 32 are similar. Although not shown, a portion of the first opening 30 and the second opening 32 can be formed by the base connector 20. This occurs when the first opening 30 and the second opening 32 are larger in size, so they overlap both the base connector 20 and one of the projections 12, 16.

The recess 22 of the base connector 20 is positioned between the first nostril projection 12 and the second nostril projection 16. The septum 100 of the nose 102 rests within the recess 22. The septum 100 separates the first nostril 104 and the second nostril 106 of the nose 102. The recess base 26 needs a sufficient height 'h' to fully accept the septum 100, thus allowing the first nostril projection 12 and second nostril projection 16 to adequately protrude into the first nostril 104 and second nostril 106. Adequate protrusion into the nostril is necessary to apply the appropriate pressure to the proper place on the tissue of the nose 102. The recess base 26 is positioned near the face, where the recess base 26 accepts the back of the septum 100. The recess gap 28 is an open area between the first nostril projection 12 and second nostril projection 16. Since the recess gap 28 is fully open, it does not impede higher and deeper placement of the first tip 38 and second tip 40 within the nostrils.

Figure 3:
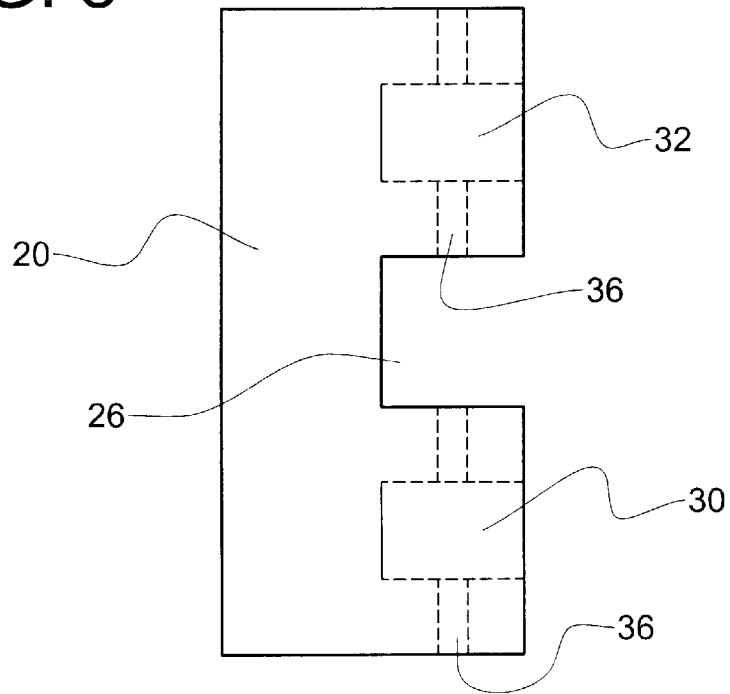
FIG. 3 is a back view of the device, with the openings and apertures shown in dashed lines.

FIG. 3 shows a back view of the device, illustrating the base connector 20. The recess base 26 separates the first nostril projection 12 and the second nostril projection 16. The recess base 26 accepts the back of the septum 100 of the nose 102, so the first nostril projection 12 and the second nostril projection 16 can be positioned up inside the nose 102. Although not visible from this view, the apertures, the first opening 30 and second opening 32 are illustrated in dashed lines.

Figure 4:
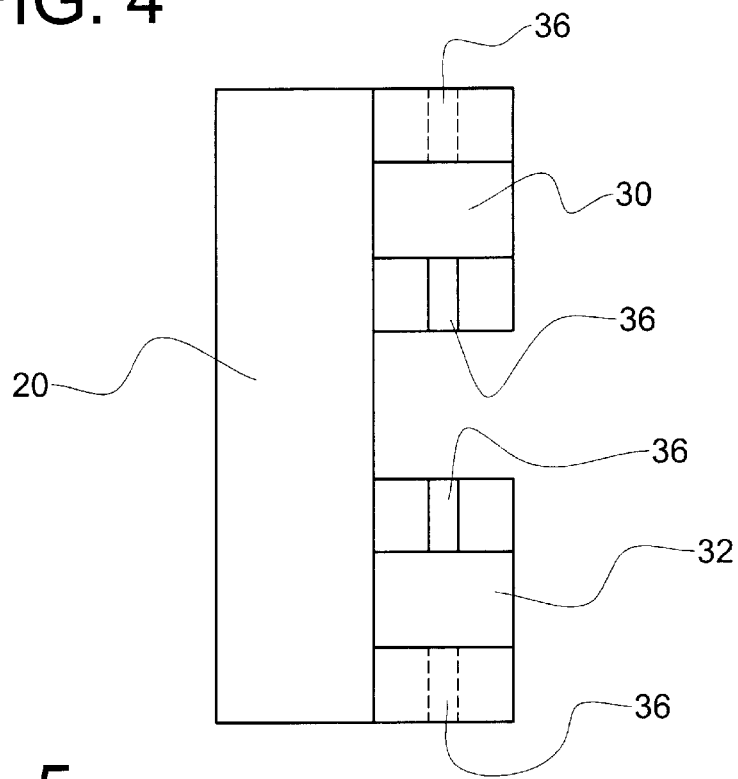
FIG. 4 is a cutaway view along the 4—4 line of FIG. 1.

Referring to FIG. 4, which is a cutaway view along the 4—4 line of FIG. 1. The cutaway view exposes the first opening 30, second opening 32, and some of the apertures 36. The first opening 30 cuts through the first nostril projection 12, and the second opening 32 cuts through the second nostril projection 16. Apertures 36 travel from the first opening 30 and second opening 32 to the recess 22. Other apertures 36 shown in dashed lines travel from the first opening 30 and second opening 32 to the exterior of the device. The base connector 20 is below the first nostril projection 12 and the second nostril projection 16.

Figure 5:
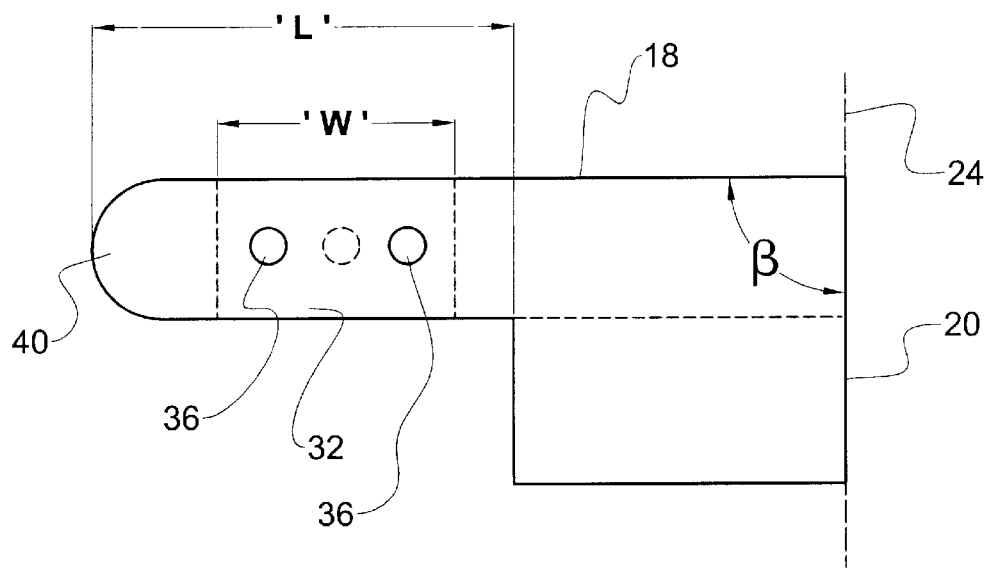
FIG. 5 is a side view of the device, with the openings and apertures shown in dashed lines.

FIG. 5 is a side view of the device. The base connector 20 has a vertical axis 24. The vertical axis 24 and the second nostril projection 16 form the angle β, which is about ninety degrees. An angle β of about ninety degrees causes the nose 102 to be extended. The first nostril projection 12 is hidden from view behind the second nostril projection 16. Apertures 36 travel from the second opening 32 to the exterior of the device. The second opening 32 is shown with dashed lines. The aperture traveling from the second opening 32 to the recess gap 28 is shown in dashed lines.

Referring particularly to FIGS. 6–10, different angles α and angles β are illustrated. The invention is wedged into place in the nose 102. The backside of the base connector 20 is placed against the face 110. A portion of the base connector 20 protrudes into the nose 102, since the recess base 26 accepts some of the septum 100. The first tip 38 and second tip 40 apply pressure to the inside of the first nostril 104 and the second nostril 106, near the nostril end. The invention receives support and pressure from two directions. First the person's face supports the base connector 20. Secondly, the inside of the first nostril 104 supports the first tip 38 and the inside of the second nostril 106 supports the second tip 40. The pressure from two directions on the nose end-adjusting device 10 holds the device 10 firmly in position.

The angles α and β can be greater than ninety degrees, which causes the nose 102 to be lifted. Alternately, the angles α and β can be less than ninety degrees, which causes the nose 102 to be lowered. When the nose 102 is lowered, the base recess 22 needs to have a greater height 'h'. A greater height 'h' allows the nose 102 end-adjusting device to be placed higher in the nose 102, so that the first tip 38 and second tip 40 remain in the nostrils.

Figure 6:
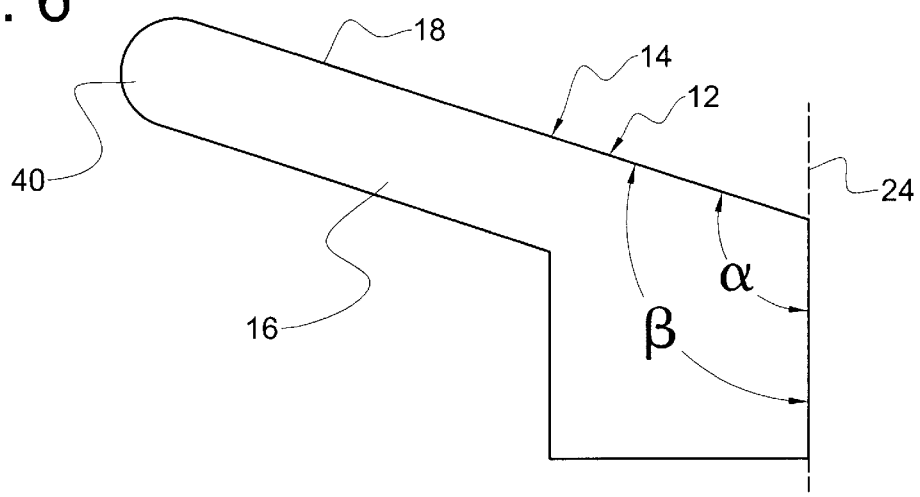
FIG. 6 is a side view, with an angle of about one hundred and twenty degrees for raising the nose end.
Figure 9:
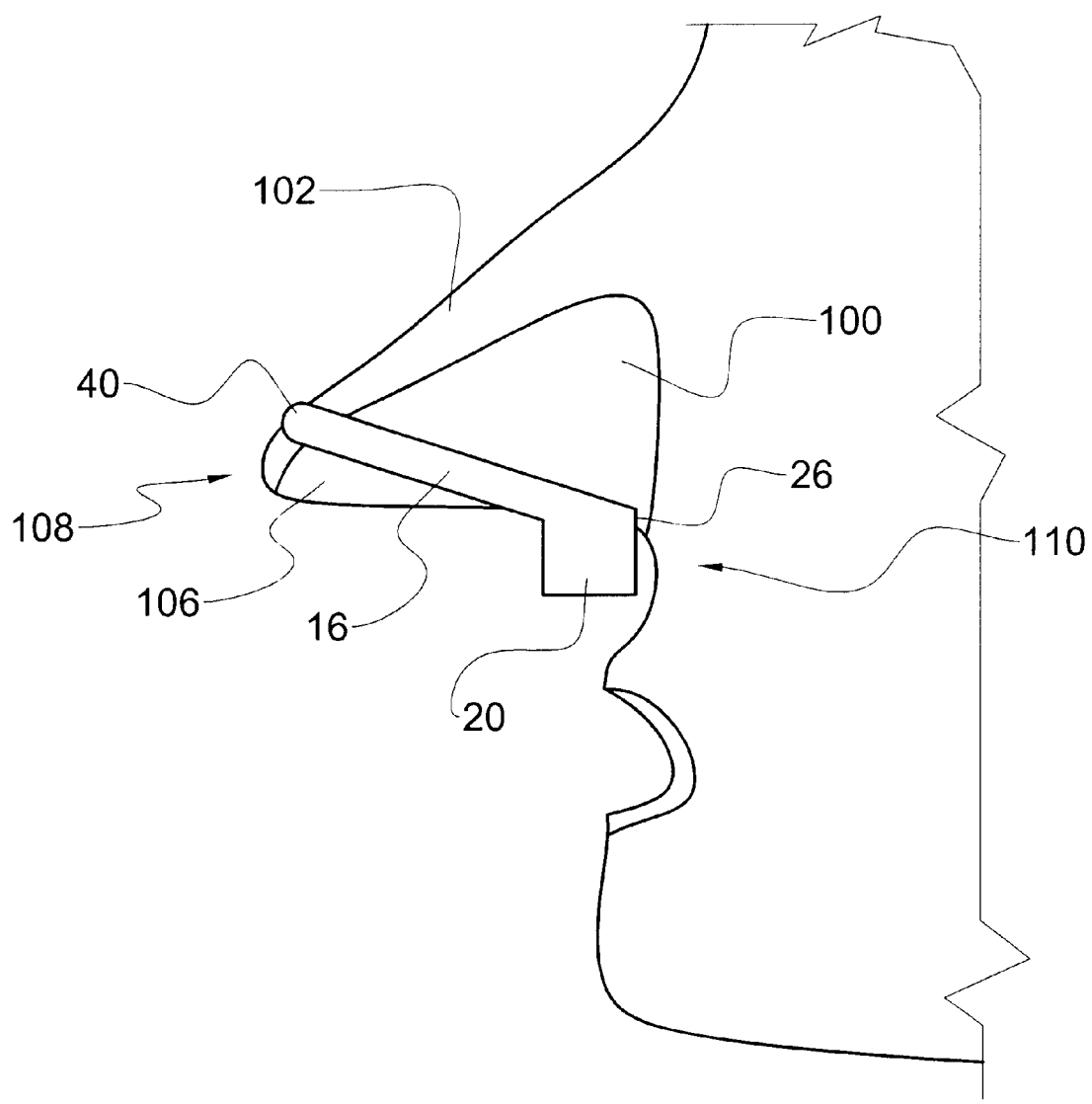
FIG. 9 illustrates the device in application as a nose raising device.

Referring to FIGS. 6 and 9, the angles α and β are greater than ninety degrees, which causes the nose 102 to be lifted. FIG. 6 shows an angle α and angle β of about one hundred and twenty degrees. When the nose 102 is raised, the base recess 22 does not need to have as great of a height 'h'. The base connector 20 can be placed lower in the nose 102, with the first tip 38 and second tip 40 protruding higher into the nostrils. The highest part of the recess base 26 is below the highest part of the first tip 38 and second tip 40.

When the nose 102 is raised and the angles α and β are greater than ninety degrees, then more of the base connector 20 can be outside of the nostrils. The greater the angle α and β, the higher into the nose 102 the first projection and second projection can protrude. Typically the first tip 38 and second tip 40 are placed about the nose end 108. This placement applies pressure to the portion of the nose 102 that is most susceptible to movement and modification. FIG. 9 illustrates a nose 102 raising application of the nose end-adjusting device. The base connector 20 protrudes partially into the nose 102, while resting against the face, below the nose 102. The recess base 26 is not as deep, with more of the base connector 20 visible outside of the nose 102.

Figure 7:
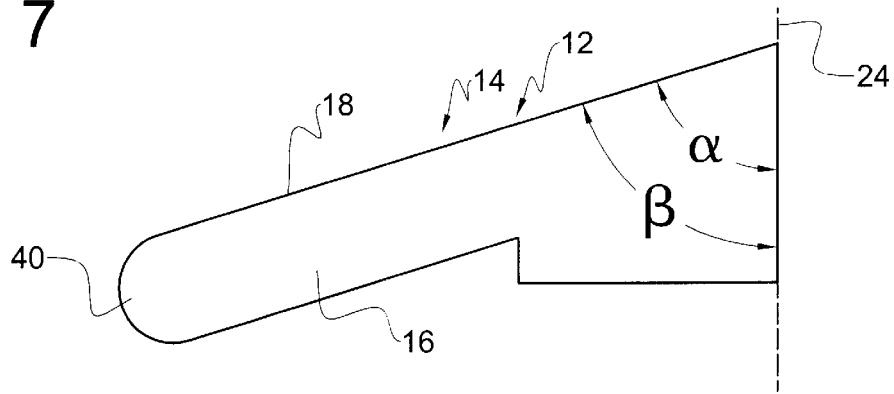
FIG. 7 is a side view, with an angle of about sixty degrees for lowering the nose end.
Figure 8:
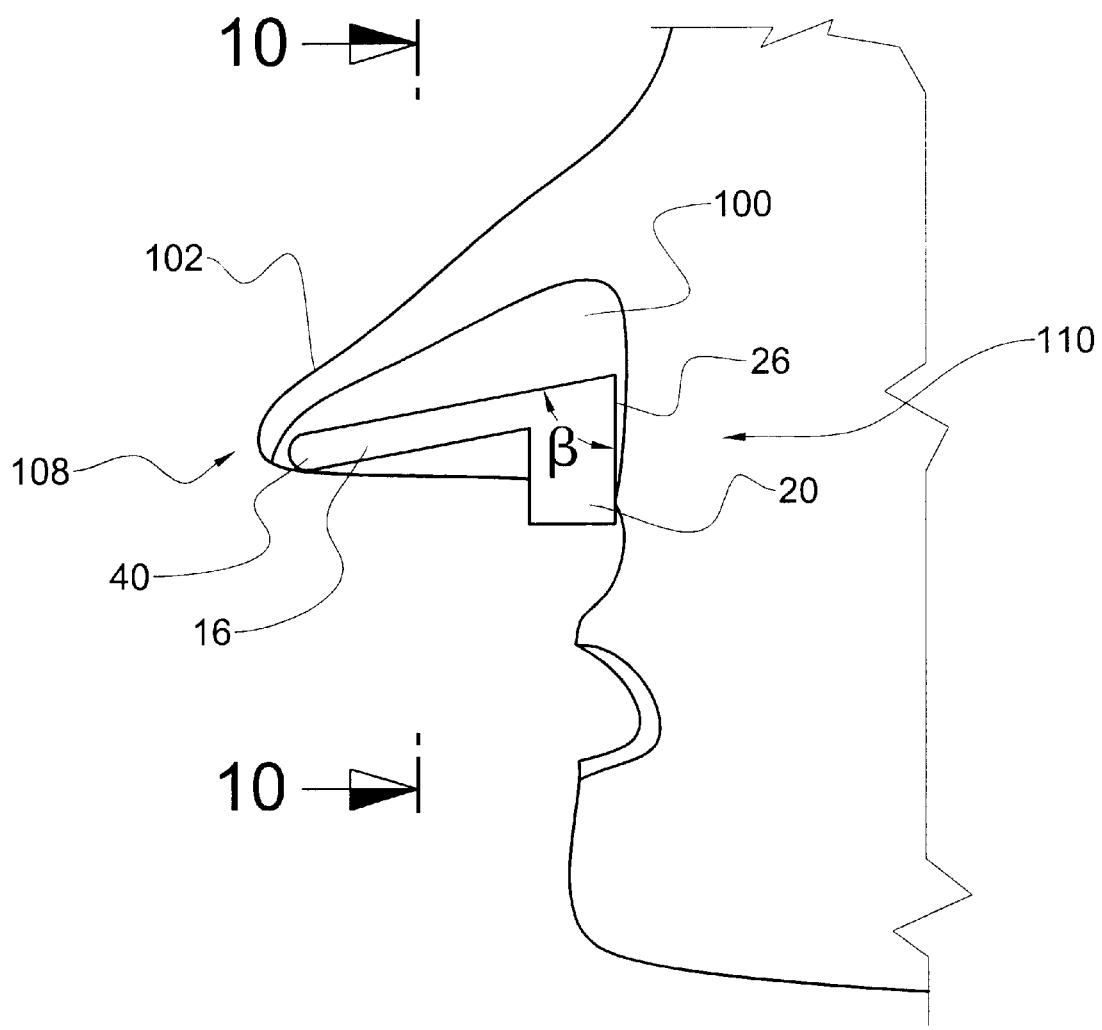
FIG. 8 is a side view that illustrates the application of the nose end-adjusting device within the nose, as a nose lowering device.
Figure 10:
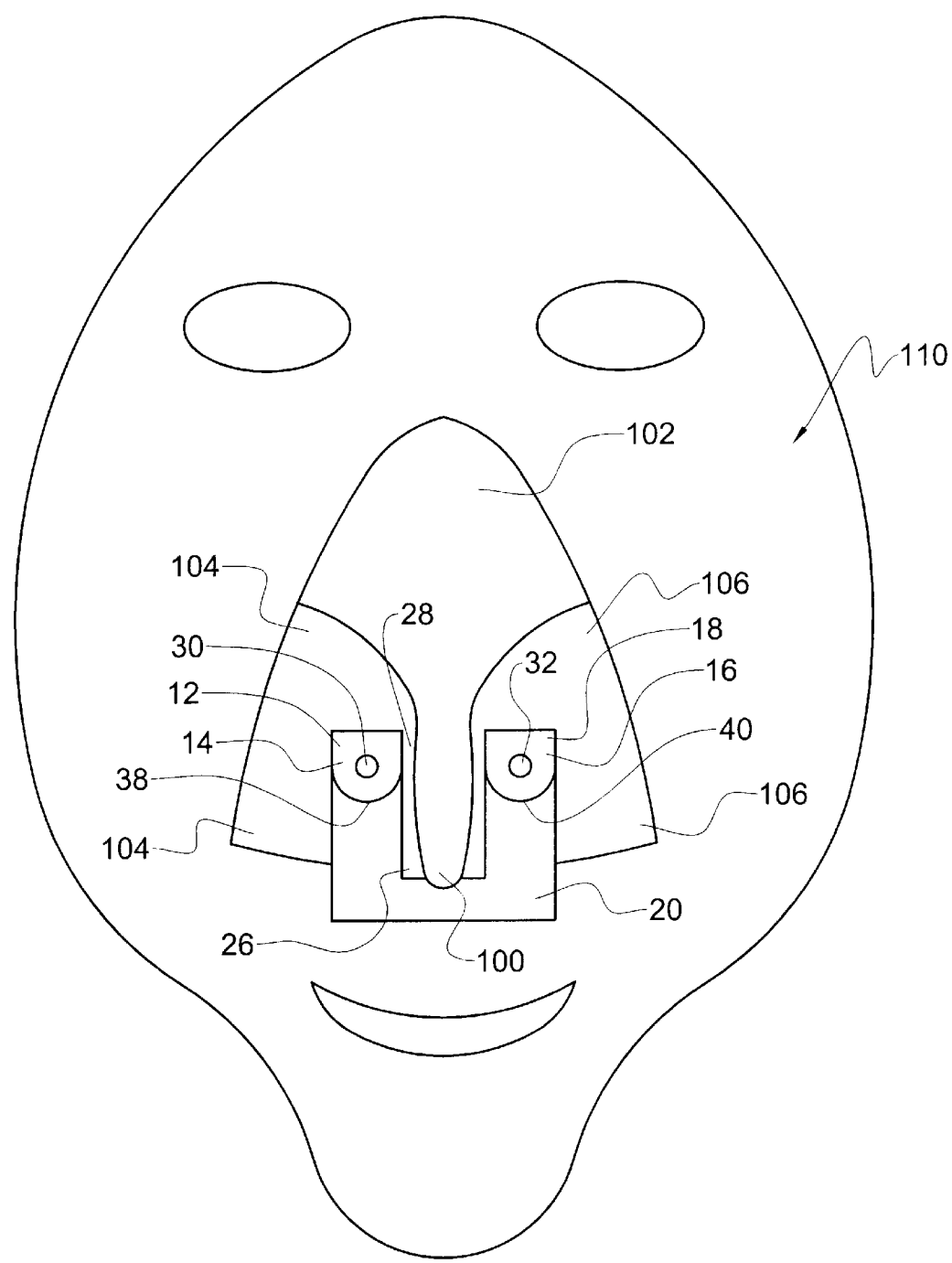
FIG. 10 shows a cutaway view along the 10—10 line of FIG. 8.

Referring particularly to FIGS. 7, 8 and 10, the angles angle α and β can be less than ninety degrees, so the highest part of the recess base 26 is above the highest part of the first tip 38 and second tip 40. FIG. 7 shows an angle α and β of about sixty degrees. A deep recess base 26 with a substantial height 'h' allows the base connector 20 to be positioned high in the nose 102, thus applying downward pressure on the nose 102 by the first tip 38 and second tip 40. When angles α and β are small, then the higher into the nose 102 that the recess base 26 needs to recess, to allow the first tip 38 and second tip 40 to also remain inside the nose 102. The first tip 38 and second tip 40 are below the uppermost portion of the base connector 20, since the first upper surface 14 and the second upper surface 18 slant downward.

Figure 7A:
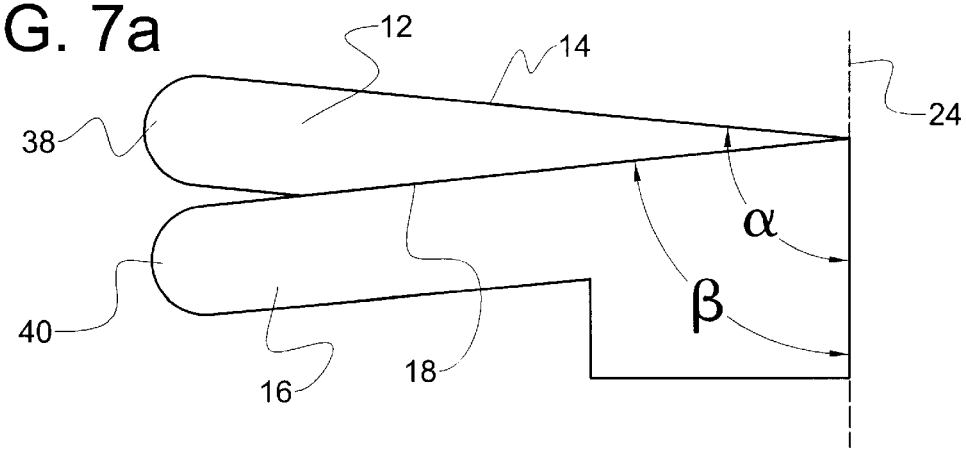
FIG. 7a is a side view, with different angles for the first projection and the second projection.

FIG. 7a is a side view, with different angles for the first nostril projection 12 and the second nostril projection 16. For some users, the nose 102 can be slightly misproportioned between the first nostril 104 and the second nostril 106. A nose end-adjusting device 10 with different angles angle α and β can be most advantageous for such a situation. The first tip 38 of the first nostril projection 12 applies appropriate pressure to the first nostril 104. Correspondingly, the second tip 40 of the second nostril projection 16 applies a different angle of pressure to the second nostril 106. Angles α and β are about ninety degrees, although they are different angles.

FIG. 8 illustrates the application of the nose end-adjusting device 10 within the nose 102, as a nose 102 lowering device. The base connector 20 protrudes partially into the nose 102, while resting against the face 110, partially below the nose 102. The second nostril projection 16 extends from the base connector 20 to about the nose end 108. The second tip 40 applies downward pressure to the nose end 108. Frequent and prolonged usage of the nose end-adjusting device 10 gradually and continuously lowers the nose end 108 to a more desirable facial profile.

FIG. 10 shows a cutaway view along the 10—10 line of FIG. 8. The back end of the device rises above the first tip 38 and the second tip 40, since the first upper surface 14 and the second upper surface 18 slant downward. The base connector 20 is visible below the first tip 38 and the second tip 40. The recess gap 28 and the recess base 26 are between the first nostril projection 12 and the second nostril projection 16. The first nostril projection 12 applies downward pressure to the first nostril 104 and the second nostril projection 16 applies downward pressure to the second nostril 106.

Although the present invention has been described in considerable detail with regard to the preferred versions thereof, other versions are also possible. Therefore, the appended claims should not be limited to the descriptions of the preferred versions contained herein.

In the claims:

1. A nose end adjusting device comprising:
   a) a first nostril projection having a first upper surface;
   b) a second nostril projection having a second upper surface; and
   c) a base connector having a recess and a vertical axis, wherein the recess having a recess base and a recess gap, wherein the base connector is attached to the first nostril projection and the second nostril projection, wherein the recess base accepts the back of the septum of a nose, wherein the recess gap accepts the end of the septum of the nose;
   wherein the vertical axis and the first upper surface form an angle α, wherein the vertical axis and the second upper surface form an angle β, wherein the angle α and angle β are less than about ninety degrees wherein when the first nostril projection is inserted into a first nostril of the nose, the first nostril projection applies pressure to the first nostril, such that the first nostril and the nose are lowered, wherein when the second nostril projection is inserted into a second nostril, the second nostril projection applies pressure to the second nostril, such that the second nostril and the nose are lowered.

2. The nose end adjusting device of claim 1 wherein the first projection has a first opening, and wherein the second projection has a second opening, such that air is inhaled and exhaled through the first opening and the second opening.

3. The nose end adjusting device of claim 2 wherein the first projection and the second projection have sides, wherein the sides have apertures, whereby air is inhaled and exhaled through the apertures.

4. The nose end adjusting device of claim 3 wherein the angle α is about sixty degrees.

5. The nose end adjusting device of claim 4 wherein the recess base has a height 'h', wherein the height 'h' is about 5/16 of an inch.

6. The nose end adjusting device of claim 5 wherein the first projection has a length 'L', wherein the length 'L' is about 9/16 of an inch.

7. The nose end adjusting device of claim 2 wherein the angle α is about ninety degrees.

* * * * *